United States Patent
Bacher

(10) Patent No.: US 7,014,649 B2
(45) Date of Patent: Mar. 21, 2006

(54) MEDICAL INSTRUMENT

(75) Inventor: Uwe Bacher, Tuttlingen (DE)

(73) Assignee: Karl Storz GmbH & Co. KG (DE)

( * ) Notice: Subject to any disclaimer, the term of this patent is extended or adjusted under 35 U.S.C. 154(b) by 260 days.

(21) Appl. No.: 10/659,955

(22) Filed: Sep. 11, 2003

(65) Prior Publication Data

US 2004/0127890 A1 Jul. 1, 2004

Related U.S. Application Data

(63) Continuation of application No. PCT/EP02/02490, filed on Mar. 7, 2002.

(30) Foreign Application Priority Data

Mar. 12, 2001 (DE) .......................... 101 11 766

(51) Int. Cl.
A61B 17/28 (2006.01)

(52) U.S. Cl. ...................................... 606/205; 606/208
(58) Field of Classification Search ................. 606/205, 606/206, 207, 208, 209
See application file for complete search history.

(56) References Cited

U.S. PATENT DOCUMENTS

| | | | | |
|---|---|---|---|---|
| 5,170,800 A | 12/1992 | Smith et al. | ................ | 128/751 |
| 5,263,967 A | 11/1993 | Lyons, III et al. | ........... | 606/205 |
| 5,308,358 A | 5/1994 | Bond et al. | ................ | 606/205 |
| 5,354,312 A | 10/1994 | Brinkerhoff et al. | ........ | 606/207 |
| 5,366,466 A | 11/1994 | Christian et al. | ............ | 606/174 |
| 5,496,347 A | 3/1996 | Hashiguchi et al. | ......... | 606/205 |

FOREIGN PATENT DOCUMENTS

| | | |
|---|---|---|
| DE | 299 11 011 | 10/1999 |
| EP | 0 588 658 | 3/1994 |
| EP | 0 647 433 | 4/1995 |
| EP | 0 813 843 | 12/1997 |
| EP | 1 066 798 | 1/2001 |
| WO | WO 01/19261 | 3/2001 |

*Primary Examiner*—Rosiland Rollins
(74) *Attorney, Agent, or Firm*—St. Onge Steward Johnston & Reens LLC

(57) ABSTRACT

The invention relates to a medical instrument with a shaft having on its proximal end a handle consisting of two gripping members and on its distal end a tool consisting of two jaw members that can rotate with respect to one another around a common rotation point, whereby the jaw members are rotated for opening and closing the tool by means of a push pin which is connected on the proximal end with a gripping member of the handle which is configured to be rotatable and which on the distal end is connected with each of the jaw members by means of one toggle joint. In order to design a medical instrument of the aforementioned type in such a way that it can be employed even under cramped space conditions and with sufficient power transmission, the invention proposes that the pivot points of the toggle joints are mounted on the respective jaw member at a distance from the proximal end of the jaw members, close to the common rotation point of the jaw members, and that they lie, even at maximum opening, inside the distal-end outer diameter of the shaft immediately surrounding the push pin, and that each toggle joint is mounted over just one pivot point on the push pin, where the pivot point of the one toggle joint lies on the push pin above the center axis of the push pin and the pivot point of the other toggle joint lies on the push pin below the center axis of the push pin, and that the toggle joint, and whereby the distal end of the push pin connected with the toggle joints is two-armed in configuration, where the pivot points of the toggle joins are arranged on the front ends of the arms and one arm is configured as jointed away from the center axis of the push pin upwards, and the other arm is configured as jointed away from the center axis of the push pin downwards.

1 Claim, 2 Drawing Sheets

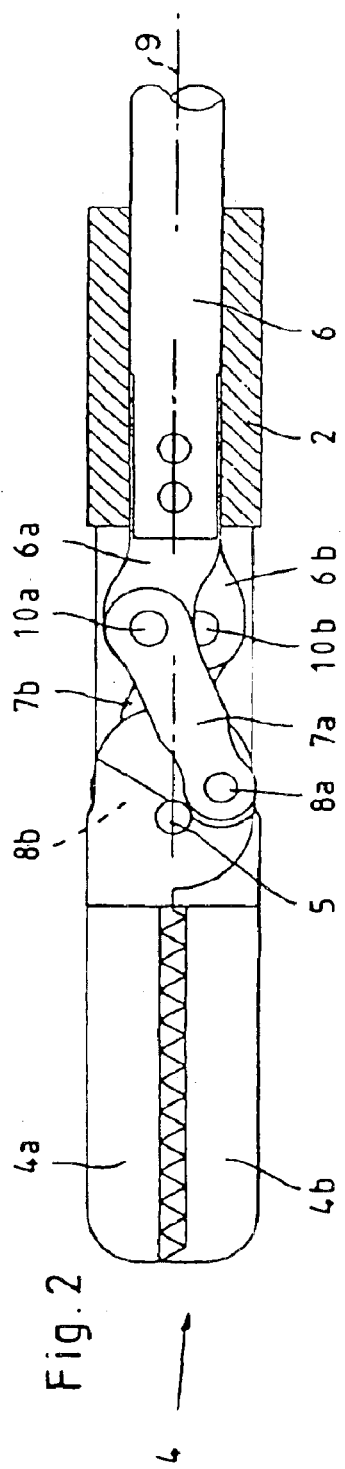
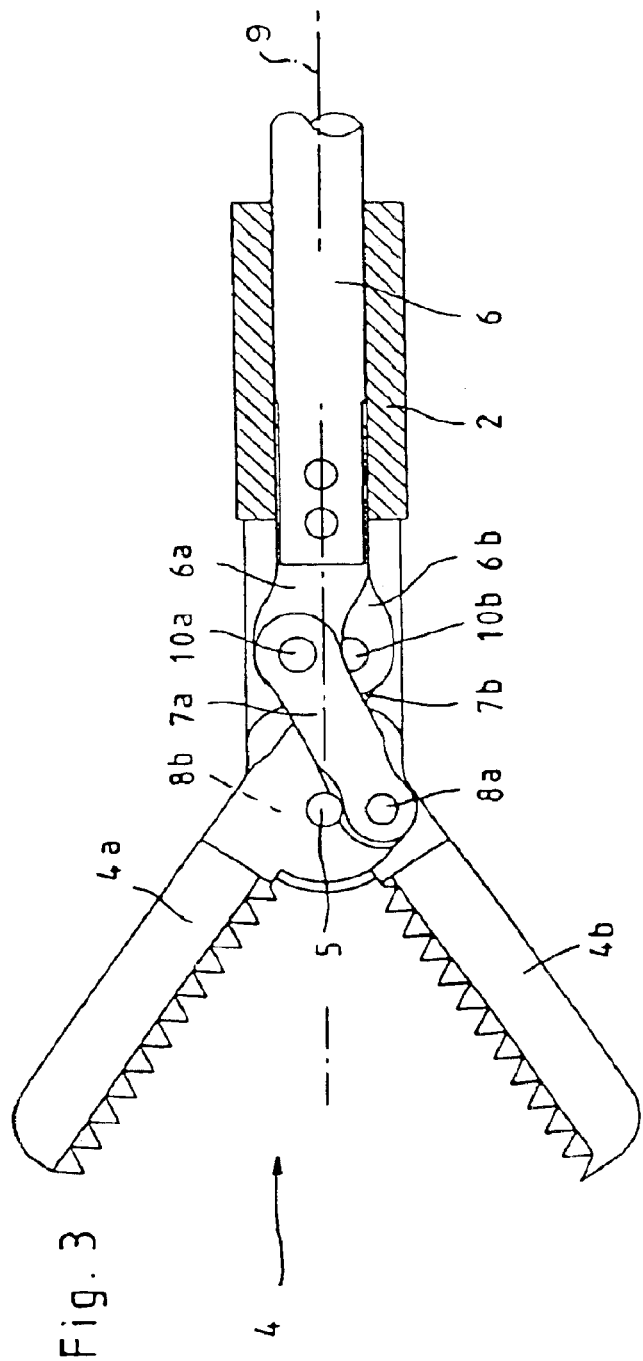

MEDICAL INSTRUMENT

This application is a continuation of pending International Patent Application No. PCT/EP02/02490 filed on Mar. 7, 2002 designating the United States and claiming priority of pending German Patent Application No. 101 11 766.0 filed on Mar. 12, 2001.

FIELD OF THE INVENTION

The invention relates to a medical instrument with a shaft having on its proximal end a handle consisting of two handle members and on its distal end a tool consisting of two jaw members that can rotate with respect to one another around a common rotation point, whereby the jaw members rotate to open and close the tool by means of a push pin, which is connected on the proximal end with a gripping member configured so as to be rotatable and which on the distal end is connected with each of the jaw members by a steering lever, and where the pivot point of each steering lever is situated so close to the common rotation point of the jaw members that the pivot points lie inside the diameter of the shaft even at maximum opening.

Conventional medical instruments are in frequent practical use as gripping, securing, and/or cutting tools. The jaw members in this case can have blades in order to sever tissue, or blunt surfaces for securing separated tissue or to stanch blood vessels for instance.

A common trait of these medical instruments is that both jaw members of the tool mounted on the distal end of the shaft can be rotated around a common rotation point. A push pin is provided for opening and closing the jaw members, which push pin is connected with a movable gripping member of the handle. In order to be able to rotate two jaw members by means of a single push pin, the jaw members and the push pin are connected to one another by means of one toggle joint each, and each of these levers are connected on the one hand by joints with the push pin and on the other hand by joints with the respective jaw member.

A medical instrument of this kind is known, for instance, from DE 299 11 011 U. In this known medical instrument the pivot points of the toggle joint lie on the respective jaw member at some distance from the common rotation point of the jaw members, so that upon sliding the push pin, especially for closing the tool, a lever ratio results that allows sizable power transmission. These medical instruments have proven their usefulness in practice; however, under cramped space conditions they have the disadvantage that the toggle joints rotate outward when the jaw members open and thus they clearly increase the diameter of the instrument in the area between the push pin and the tool. This extra required space is not always available, however, and therefore these known instruments cannot be employed for all operations.

Consequently it is the task of the invention to design a medical instrument of the aforementioned type in such a way that it can be employed even under cramped space conditions and with sufficient power transmission.

The invention fulfills this aim in that the pivot points of the toggle joints on the respective jaw member are arranged at a distance from the proximal end of the jaw members, close to the common rotation point of the jaw members and, even at maximum opening, inside the distal-end outer diameter of the shaft immediately surrounding the push pin, and in that each toggle joint is mounted over just one pivot point on the push pin, where the pivot point of the one toggle joint lies on the push pin above the center axis of the push pin and the pivot point of the other toggle joint lies on the push pin below the center axis of the push pin, and in that the distal end of the push pin connected with the toggle joints is configured as two-armed, where the pivot points of the toggle joints are mounted on the front ends of the arms and one arm is configured as jointed upward away from the center axis of the push pin and the other arm as jointed downward away from the center axis of the push pin.

By situating the pivot points of the toggle joint on the jaw members at the common rotation point of the jaw members, an instrument is made available both of whose jaw members can be rotated by means of one push pin and which can also be used in cramped space conditions, because the pivot points, due to the close proximity to the common rotation point, are not rotated so far outward, even at maximum opening, that they extend beyond the pre-established diameter of the shaft. Because the lever ratio and thus, in particular, the power that can be applied upon closing the tool have worsened in relation to state-of-the-art instruments because of the displacement of the pivot points toward the common rotation point, the pivot point of the one toggle joint is situated on the push pin above the center axis of the push pin and the pivot point of the other toggle joint on the push pin is situated below the center axis of the push pin. By means of this displacement of the pivot points between the toggle joints and the push pin away from the center axis, the lever ratio responsible for the possible power transmission can be further improved so that cutting operations can also be performed reliably.

Finally, it is proposed with the invention that the distal end of the push pin connected with the toggle joints is configured to have two arms whereby the pivot points of the toggle joint are arranged on the front ends of the arms and one arm is designed as jointed upward away from the center axis of the push pin and the other arm is designed as jointed downward away from the center axis of the push pin. By thus spreading apart the distal end of the push pin connected with the toggle joints, the lever ratio can be even further improved.

BRIEF DESCRIPTION OF THE DRAWINGS

Additional characteristics and advantages can be seen from the following description of the associated drawing, in which an embodiment of an inventive medical instrument is presented merely schematically by way of example. The illustrations are as follows:

FIG. 2 Enlarged and partly cut out view of detail II according to FIG. 1, showing the jaw members in closed position FIG. 3 Enlarged and partly cut out view of detail III according to FIG. 1, showing the jaw members in open position.

DETAILED DESCRIPTION OF THE DRAWINGS

Figure 1:
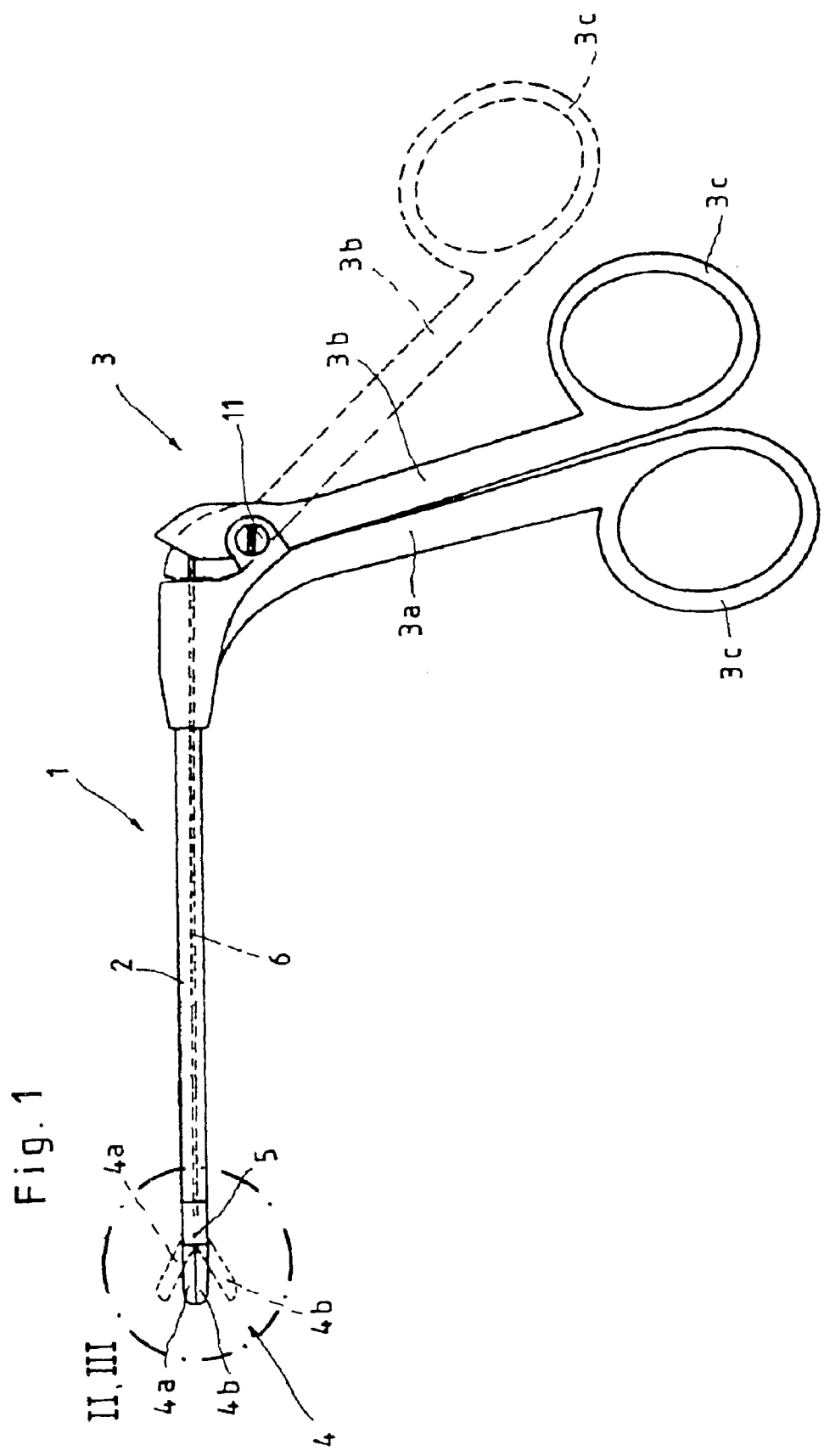
FIG. 1 Lateral view of an inventive medical instrument

FIG. 1 shows a lateral view of a medical instrument, whose power transmission mechanism has multiple uses, such as for punching, cutting, holding a needle, as grasping tool, and the like. The illustrated medical instrument 1 consists essentially of a hollow shaft 2 on whose proximal end a handle 3 is mounted, consisting of a rigid gripping part 3a and a gripping part 3b that can rotate with respect to the rigid gripping part 3a. On the distal end of the shaft 2 a tool 4 is mounted, which is configured by two jaw members 4a and 4b that can rotate with respect to one another around a common rotation point 5. As can be seen from the detailed views in FIGS. 2 and 3, as well as the complete view of FIG. 1, the jaw members 4a and 4b of the tool 4 and the rotatable gripping part 3b of handle 3 are connected to one another by means of a push pin 6 in such a way that, by displacing the gripping member 3b, the jaw members 4a and 4b can be moved from the closed position (striped areas in FIGS. 1 and 2) into the open position (dot-and-dash areas in FIGS. 1 and 2) or vice versa. Each corresponding position of the rotatable gripping member 3b in FIG. 1 is likewise striped (for the closed position) and marked with dots and dashes (for the open position). As can also be seen from the detail views of FIGS. 2 and 3, the push pin 6 is not connected directly with the jaw members 4a and 4b but by means of two toggle joints 7a and 7b. The toggle joints 7a and 7b make it possible to displace both jaw members 4a and 4b with just one push pin 6 and also to ensure sufficient power transmission to the tool 4, especially upon closing the jaw members 4a and 4b.

In coupling the push pin 6 to the jaw members 4a and 4b of the tool 4 by means of the toggle joints 7a and 7b, to ensure on the one hand that sufficient cutting or adhesive power can be achieved by means of jaw members 4a and 4b, and on the other hand that the dimensions of the instrument are not increased by the lever mechanism, first the toggle joints 7a, 7b are connected with the jaw members 4a and 4b by means of the jaw members 4a, 4b, and second, the distal end of the push pin 6 is designed to be two-armed, with two arms 6a and 6b jointed away from the center axis 9 of the push pin 6.

The exact structure of the lever mechanism and the arrangement of the components to one another can be seen in FIGS. 2 and 3. The connection of the toggle joints 7a and 7b with the arms 6a and 6b of the push pin 6 proceeds by way of pivot points 10a and 10b, which are arranged above and below the center axis 9 of the push pin 6. By displacing the pivot points 10a and 10b away from the center axis 9 of the push pin rod 6, the achievable lever ratio is further increased, after having been worsened by the displacement of the pivot points 8a and 8b toward the common rotation point 5 of the jaw members 4a, 4b. This displacement of the pivot points 8a, 8b is necessary, however, because only in this way can one ensure that the pivot points 8a, 8b do not extend beyond the diameter of the shaft 2 even with maximum opening of the jaw members 4, 4b or of the toggle joints 7a, 7b.

The medical instrument is actuated as follows:

For secure gripping of the gripping members 3a, 3b of the handle 3, the latter have finger lops 3c on their free ends. In the illustrated embodiment, the gripping member 3b can be rotated around a rotation axis 11 with respect to the other, rigid gripping member 3a.

Through the coupling of the rotatable gripping member 3b by the push pin rod 6 and the toggle joints 7a, 7b with the rotatable jaw members 4a, 4b of the tool 4, the tool 4 can be opened and closed.

As can be seen in FIGS. 2 and 3, the pivot points 8a, 8b and 10a, 10b for connecting the toggle joints 7a and 7b with jaw members 4a, 4b and the arms 6a, 6b of the push pint 6 are arranged in such a way that none of the pivot points 8a, 8b or 10a, 10b extends beyond the diameter of the shaft 2 when the jaw members 4a, 4b are displaced. A medical instrument 1 of this configuration can therefore be employed even under cramped space conditions.

| Reference List | |
|---|---|
| 1 | medical instrument |
| 2 | shaft |
| 3 | handle |
| 3a | rigid gripping member |
| 3b | rotatable gripping member |
| 3c | finger loops |
| 4 | tool |
| 4a | jaw member |
| 4b | jaw member |
| 5 | rotation point |
| 6 | push pin |
| 6a | arm |
| 6b | arm |
| 7a | toggle joint |
| 7b | toggle joint |
| 8a | pivot point |
| 8b | pivot point |
| 9 | center axis |
| 10a | pivot point |
| 10b | pivot point |
| 11 | rotation axis |

What is claimed is:

1. Medical instrument with a shaft, on whose proximal end a handle consisting of two gripping members is arranged and on whose distal end a tool is mounted consisting of two jaw members that can rotate around a common rotation point with respect to one another, whereby the rotation of the jaw members for opening and closing the tool is accomplished by means of a push pin, which on the proximal side is connected with a gripping member of the handle configured to be rotatable, and which on the distal side is connected with each of the jaw members by means of a toggle joint in each case and whereby the pivot point of each toggle joint is arranged on each jaw member so close to the common rotation point of the jaw members that the pivot points lie within the diameter of the shaft even at maximum opening, whereby the pivot points of the toggle joint on the respective jaw member are mounted at a distance from the proximal end of the jaw members, close to the common rotation point of the jaw members and also at maximum opening lie within the distal-end outer diameter of the shaft immediately surrounding the push pin and whereby each toggle joint is mounted over only one respective pivot point on the push pin, where the pivot point of the one toggle joint lies on the push pin above the center axis of the push pin and the pivot point of the other toggle joint lies on the push pin below the center axis of the push pin, and whereby the distal end of the push pin connected with the toggle joints is two-armed in configuration, where the pivot points of the toggle joints are arranged on the front ends of the arms and one arm is configured as jointed away from the center axis of the push pin upwards, and the other arm is configured as jointed away from the center axis (9) of the push pin downwards.

* * * * *